US011623047B2

(12) United States Patent
Alkhatib et al.

(10) Patent No.: US 11,623,047 B2
(45) Date of Patent: Apr. 11, 2023

(54) T-SHAPED SLOT LOCKING SAFETY SYRINGE

(71) Applicant: QATAR UNIVERSITY, Doha (QA)

(72) Inventors: Sami Alkhatib, Doha (QA); Faris Tarlochan, Doha (QA)

(73) Assignee: QATAR UNIVERSITY, Doha (QA)

( * ) Notice: Subject to any disclaimer, the term of this patent is extended or adjusted under 35 U.S.C. 154(b) by 428 days.

(21) Appl. No.: 16/756,780

(22) PCT Filed: May 29, 2019

(86) PCT No.: PCT/IB2019/054462
§ 371 (c)(1),
(2) Date: Apr. 16, 2020

(87) PCT Pub. No.: WO2020/240259
PCT Pub. Date: Dec. 3, 2020

(65) Prior Publication Data
US 2021/0113771 A1  Apr. 22, 2021

(51) Int. Cl.
*A61M 5/31* (2006.01)
*A61M 5/32* (2006.01)
*A61M 5/50* (2006.01)

(52) U.S. Cl.
CPC ........ *A61M 5/3134* (2013.01); *A61M 5/3202* (2013.01); *A61M 5/50* (2013.01)

(58) Field of Classification Search
CPC .. A61M 5/3134; A61M 5/3202; A61M 5/315; A61M 5/50; A61M 2005/323; A61M 2005/3224
See application file for complete search history.

(56) References Cited

U.S. PATENT DOCUMENTS

| | | | | |
|---|---|---|---|---|
| 5,415,638 | A | * | 5/1995 | Novacek ............. A61M 5/5086 604/110 |
| 7,947,020 | B2 | | 5/2011 | Thayer |
| 2004/0176730 | A1 | * | 9/2004 | Wang ................ A61M 25/0631 604/263 |
| 2008/0281266 | A1 | * | 11/2008 | Walton ................ A61M 5/5013 604/110 |

OTHER PUBLICATIONS

International Search Report and Written Opinion of the International Searching Authority in corresponding International Application No. PCT/IB2019/054462 dated Oct. 17, 2019.

\* cited by examiner

*Primary Examiner* — Tasnim Mehjabin Ahmed
(74) *Attorney, Agent, or Firm* — Squire Patton Boggs (US) LLP

(57) ABSTRACT

To prevent accidental needle stick injuries, a syringe has a plunger configured to pull the syringe into the syringe barrel after clinical use. The syringe has an additional safety feature that restricts subsequent movement of the plunger. After the needle has been retracted in its entirety within the barrel of the syringe, movement of the plunger is restricted by a two-part locking mechanism, a notch on the plunger and a T-shaped slot on the barrel with a one-way catch section to prevent the needle tip from being pushed accidentally through the barrel wall.

17 Claims, 10 Drawing Sheets

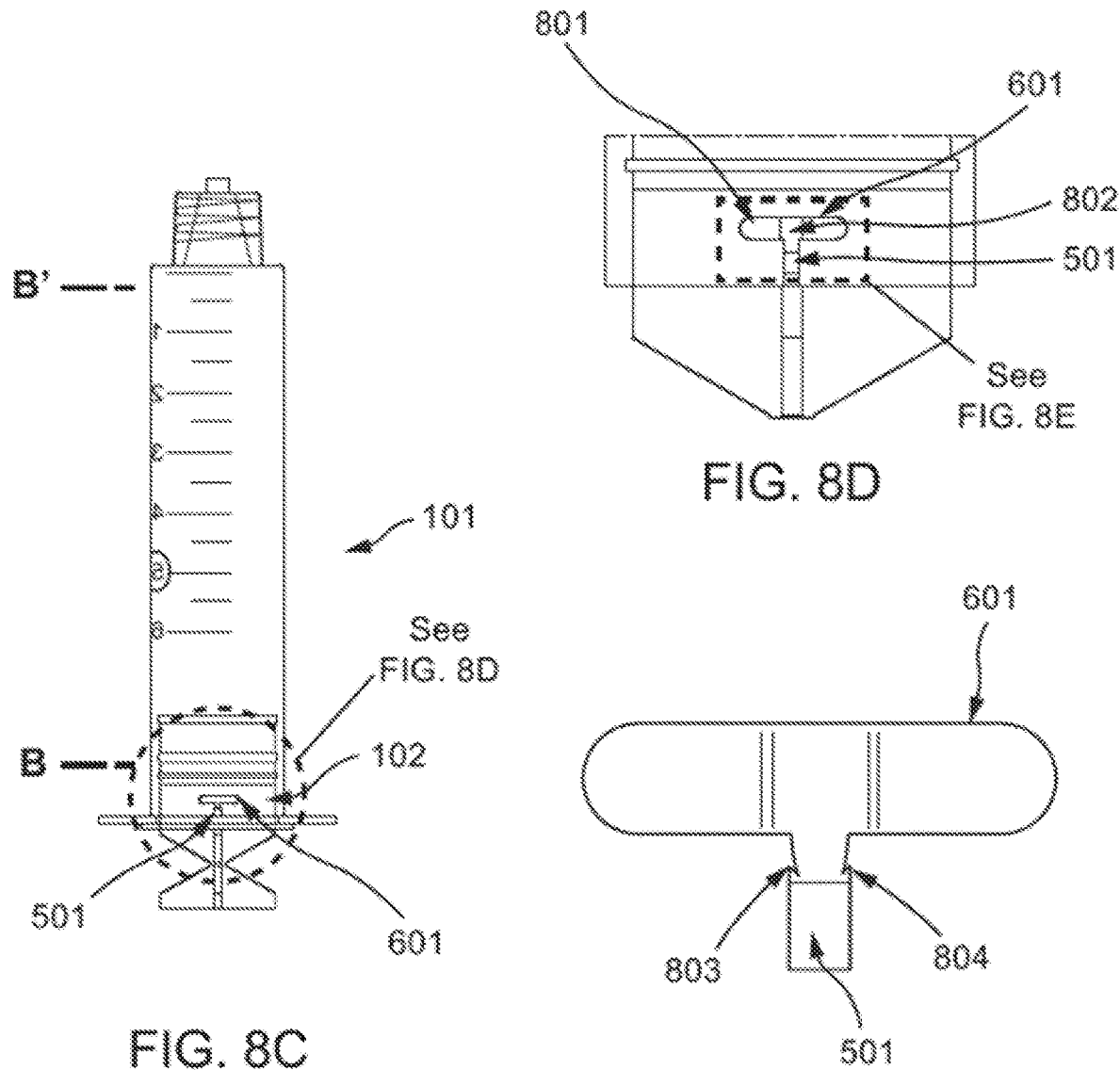

T-SHAPED SLOT LOCKING SAFETY SYRINGE

FIELD OF THE INVENTION

The present invention relates to a syringe, and more particularly to a syringe with a safety locking mechanism to prevent accidental needle stick injuries.

BACKGROUND OF THE INVENTION

Needle stick injuries are wounds caused by needles that accidentally puncture the skin. Accidental needle stick (stab) injuries or exposure of used needles and other sharp objects pose serious health risks, such as the transmission of infections and blood-borne viruses, including Human Immunodeficiency Virus (HIV) which leads to AIDS (Acquired Immune Deficiency Syndrome), hepatitis B, and hepatitis C or other viruses. Conventionally, safety syringes have a protective cap, a cylinder, a plunger and a cannula mounted on a cannula base. The cannula base may be designed such that it can be pushed firmly against a stop in the protective cap. The protective cap can be pushed externally onto a cone, corresponding to a Luer cone, of the cylinder, with a narrowed section, which is provided on the inside of the cap, in front of a recess designed for receiving the cannula base, and delimits the push on travel. The recess, which receives a cannula base may be provided with an undercut to prevent the cannula base from being removed in the forward direction and which is provided for safeguarding the cannula stop from being pushed in unintentionally during insertion of the syringe. The plunger may be designed with a section that widens the cone cylindrically and with a mushroom-shaped plunger head, which may come into pulling contact with the needle stop. A needle stick injury may occur when the cannula is retracted, however, if sufficient force is applied to the plunger to force the cannula to penetrate the walls of the barrel. Accordingly, there is a continuing need for safety features to reduce needle stick injuries.

SUMMARY OF THE INVENTION

The invention overcomes the drawbacks and disadvantages of the prior art by providing an improved safety locking mechanism to prevent the cannula from penetrating through the barrel when the cannula is retracted within the cylinder. In particular, the invention accomplishes this by:

Embodiments of the present invention may include a syringe comprising, a barrel, a cannula (needle) and a plunger. The barrel comprising a distal end and a proximate end, a medial segment between the distal end and the proximate end. The barrel interior surface extending from the distal end to the proximate end. The barrel interior surface has a first locking mechanism element between the medial segment and the distal end of the barrel. The first locking mechanism element has two catch sections formed along the external perimeter of the first locking mechanism element. Each of the two catch sections open in a single direction towards the distal end of the barrel. The barrel comprising and an opening at the proximate end.

The projecting member is configured for attachment to the proximate end of the barrel and comprises a cannula base, a cannula mounted on the cannula base, and a protective cap for covering the cannula, the cannula base and the projecting member.

The plunger comprises a first end and a second end. The plunger also comprises a plurality of ridges. The plunger comprises a second locking mechanism element along a surface of the at least one of the plurality of ridges. The second locking mechanism element increases the diameter of the plunger. The plunger is sized to pass through an opening formed at the distal end of the barrel when pressure is applied to the second end. The plunger configured to be pushed from a first position at which the first locking mechanism element is oppositely facing the second locking mechanism element, to a second position after delivery of the cylinder barrel content at which the cannula is retracted into the cylinder barrel at angle out of alignment with the opening at the proximate end. Then to a third position at which the plunger is rotated about a central axis of the plunger. The plunger being rotated within the barrel until the second locking mechanism element engages the first locking mechanism element and the second end of the plunger is pulled vertically away from the distal end of the barrel until the first locking mechanism element engages the two catch sections. The movement of the plunger, when the second locking mechanism element engages the first locking mechanism element and the two catch sections, is restricted to a region within the first locking mechanism element.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings:

FIG. 8C is a cross-section of the locking mechanisms engaged, according to certain embodiments.

FIG. 8D is an enlarged cross-section view of a portion of FIG. 8C illustrating the locking mechanisms engaged, according to certain embodiments.

FIG. 8E is an enlarged view of a portion of FIG. 8D illustrating an enlarged cross-section view of the locking mechanisms engaged, according to certain embodiments.

DETAILED DESCRIPTION OF THE INVENTION

Figure 1:
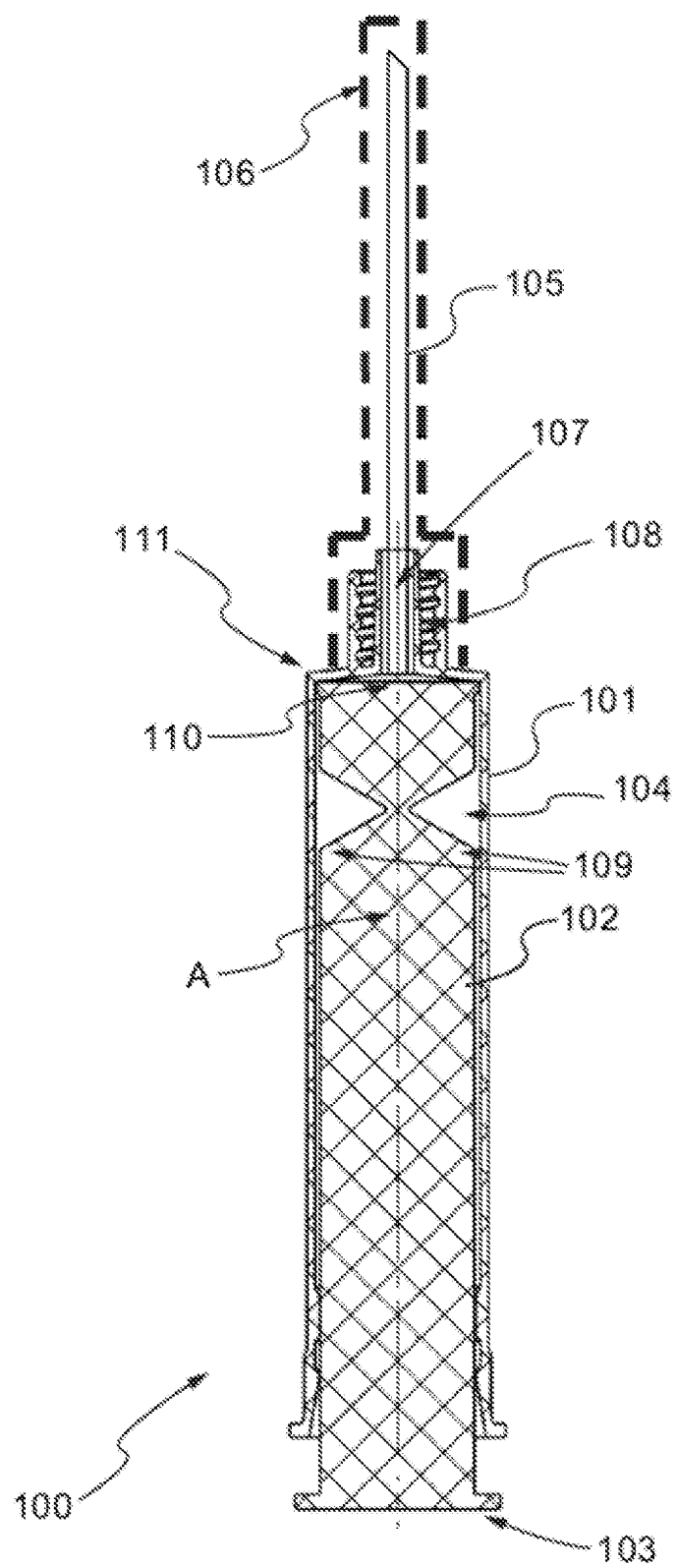
FIG. 1 is a cross-section view of a syringe with a protective cap on its proximate end, according to certain embodiments.

Referring now in more detail to the drawings for purposes of illustrating non-limiting examples, wherein like reference numerals designate corresponding or like elements among the several views, there is shown in FIGS. 1-8E an exemplary syringe 100 having a safety feature for reducing needle stick injuries.

FIG. 1, which may correspond to the state of syringe 100 during manufacturing and industrial assembly or prior to initial use. FIG. 1 shows a syringe 100, having a cylindrical tube or barrel 101, a plunger 102 with a plurality of ridges oriented axially along the surface of the plunger 102 and where each ridge may be orthogonal to the adjacent ridge, a cannula 105 mounted on a cannula base 107, which may be detachably secured to the proximate end 111 of the barrel 101 via a screw connection 108 at the proximate end 111 of the barrel 101 that may create a leak-free seal, such as, a Luer lock, with a protective cap 106 covering the cannula 105. Cannula 105, cannula base 107, and protective cap 106 are parts of a projecting member. The plunger 102 can include one or more ridges 109. The term "ridges" as used herein means a protrusion or indentation formed along the plunger 102 stem of a syringe device 100. A ridge as used herein may be of desired size, shape, dimension, elasticity, and number so as to provide tactile or sensory feedback, typically in the form of a resistive change to axial movement of the plunger within the barrel 101. The interior surface 104 of barrel 101 may be frustoconical at rear section 121 (FIG. 4) of the barrel 101. The frustoconical shape may provide a taper to facilitate initial insertion of plunger 102 into the rear section 121 (FIG. 4) of the barrel 101 during industrial assembly.

Figure 2:
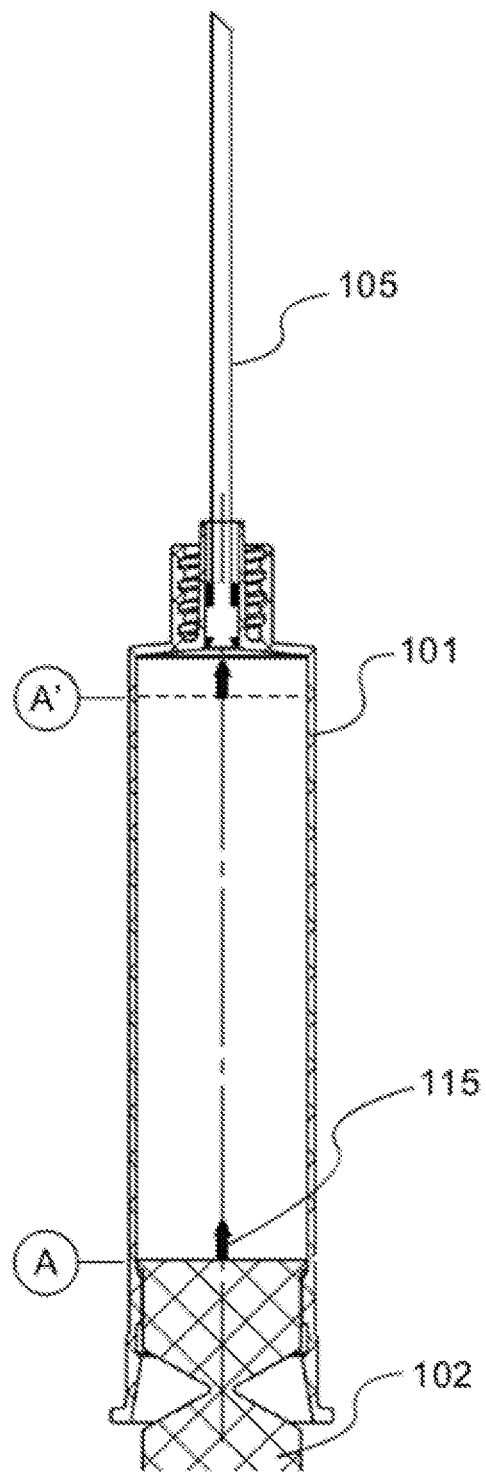
FIG. 2 is a cross-section view of a syringe with the plunger in a first position in the barrel, at which position, the distal end of the plunger is near the distal end of the barrel, according to certain embodiments.
Figure 3:
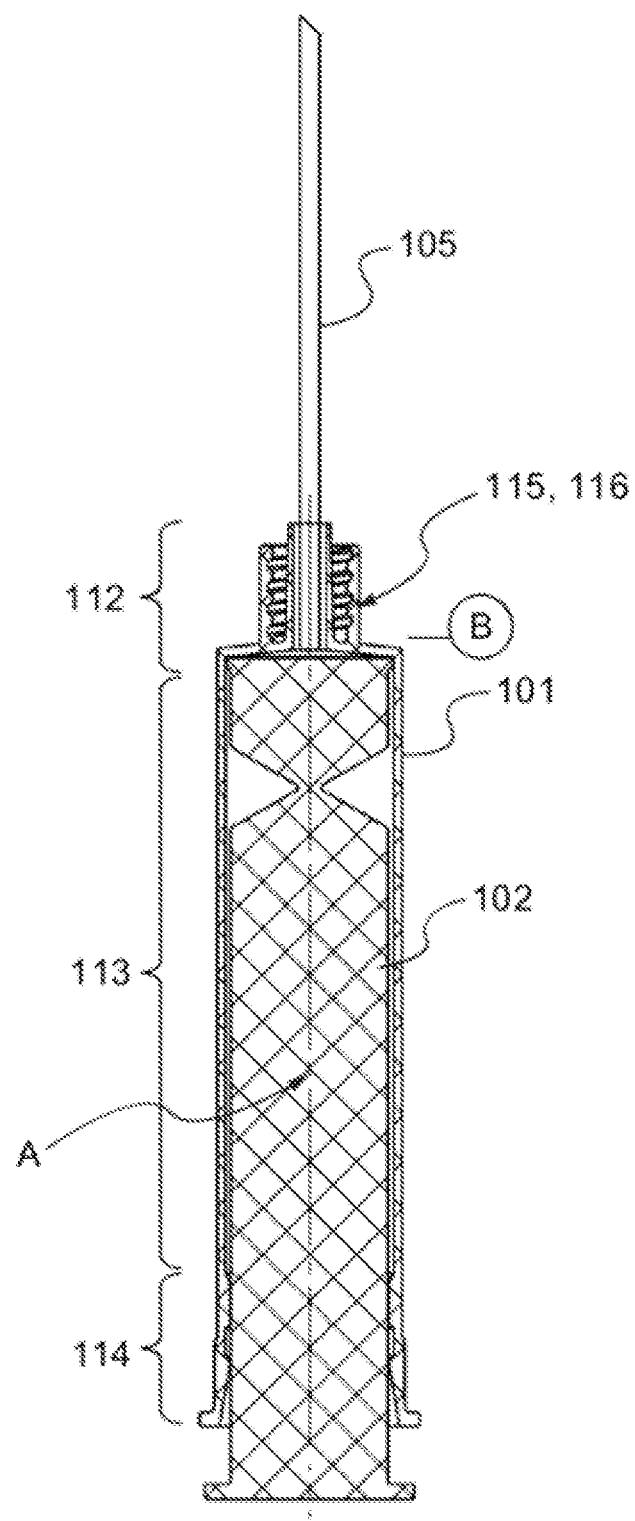
FIG. 3 is a cross-section view of a syringe with the plunger in a second position in the barrel, at which position, the top of the plunger is near the proximate end of the barrel, according to certain embodiments.
Figure 4:
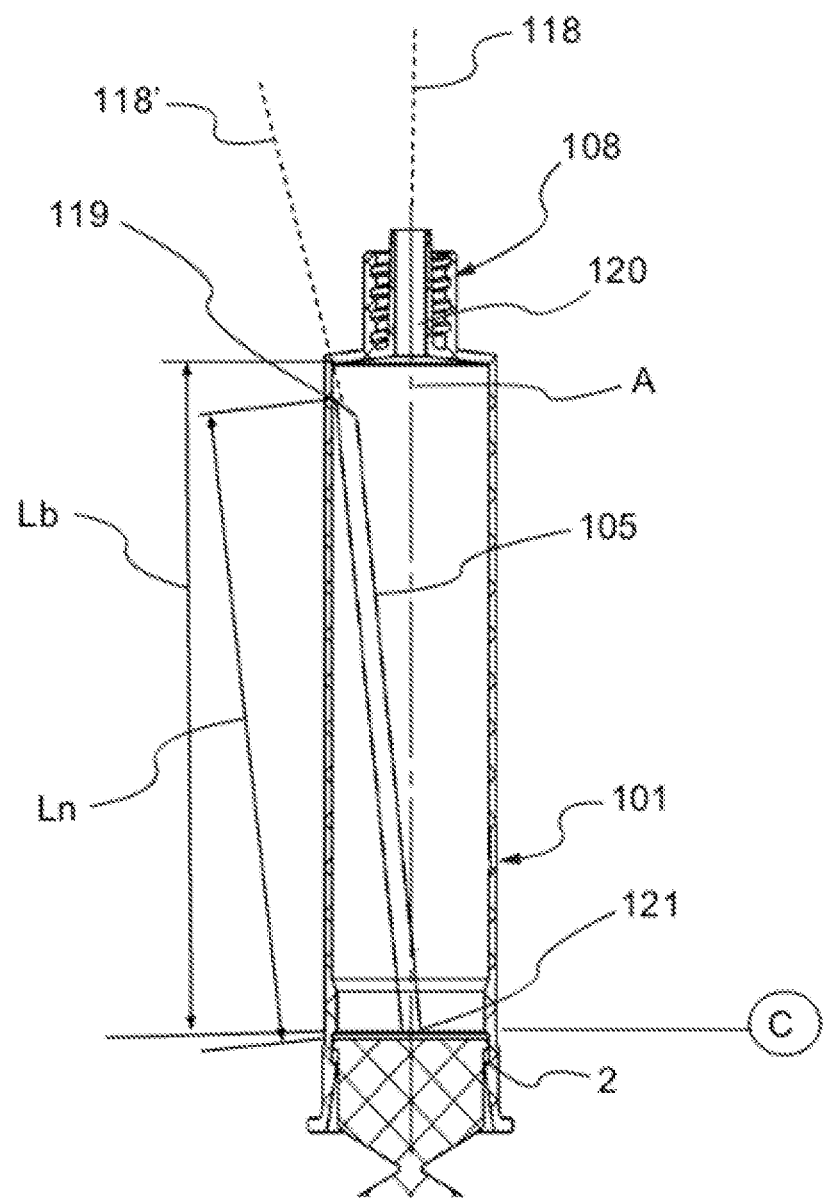
FIG. 4 is a cross-section view of a syringe showing the plunger in a third position in the barrel, at which position, the cannula is retracted within the barrel, according to certain embodiments.

FIGS. 2-4 show syringe 100 with plunger 102 at different positions within the barrel 101 with a conventional safety mechanism for retracting the cannula 105 into the cavity of the barrel 101 after use of the syringe 100. As shown in FIG. 2, the top portion 110 of plunger 102 may be moved to and from positions A and A' in order to draw fluid into the cavity within the barrel 101 through the cannula 105 and expelling such fluid from the cavity of the barrel 101 through the cannula 105. In FIG. 2, the top portion 110 of plunger 102 may be illustrated in broken lines at position A'. At position A, the top portion 110 of plunger 102 may rest on a bevel forming a slight constriction of the barrel 101, which may provide a user with tactile feedback so that the user does not inadvertently pull plunger 102 into a locked position as discussed below. Plunger 102 is sized to pass through the rear section 121 of the barrel 101. Plunger 102 comprises second catch 115 (FIG. 2), as previously mentioned. Second catch 115 is configured to attach to cannula base 107 when plunger 102 is at the second position (position B in FIG. 3). When the user retracts plunger 102 partially out of barrel 101, second catch 115 pulls cannula base 107 toward barrel rear segment 114, during which time plunger 102 is moved from the second position to the third position (position C in FIG. 4).

FIG. 3 shows syringe 100 in a second position after the user has dispensed the fluid from the cavity of the barrel 101. The top of the plunger 110 has been pushed along the center axis A of the barrel 101 to the proximate end 112 of the barrel 101, which results in second catch 115 entering cavity 116 in cannula base 107. Second catch 115 catches cannula base 107 such that when plunger 102 is retracted (pulled towards the distal end 114 of the barrel 101), as shown in FIG. 4, second catch 115 pulls cannula 105 into the cavity of barrel 101. Second catch 115 and cavity 116 are configured to allow cannula 105 to tilt off-axis, as show in FIG. 4, after cannula 105 is pulled into barrel 101 entirely. Cannula 105 may be tilt off-axis in a longitudinal central axis 118' of cannula 105 when inside barrel 101, and may not be parallel to longitudinal central axis 118 before being pulled into barrel 101. To allow for off-axis tiling, a portion of cavity 116 may be sized larger than a portion of second catch 115. With off-axis tilting, cannula tip 119 may be out of alignment with the barrel nozzle 120. If plunger 102 is somehow pushed forward, cannula tip 119 may abut shoulder wall 111 of barrel 101 and may be prevented from exiting through barrel nozzle 120.

With sufficient force applied to the bottom 103 of the plunger 102, it may be possible for the cannula 105 to pierce through the shoulder wall 111. Thus, syringe 100 possesses an additional safety mechanism, a two-part locking mechanism, described below in FIGS. 5-8E, to prevent plunger 102 from being pushed forward after cannula 105 has been retracted entirely within the cavity of barrel 101.

Figure 5:
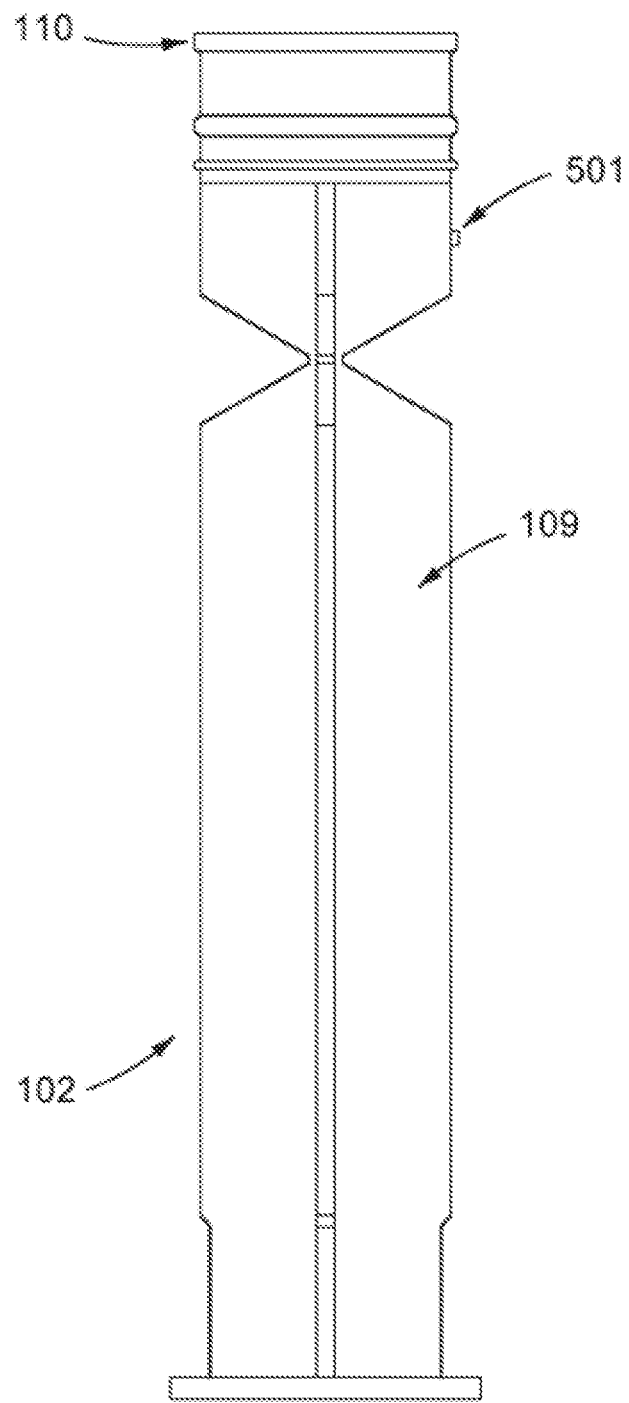
FIG. 5 is a cross-section view of a plunger with a first locking mechanism element along one of its ridges, according to certain embodiments.

As shown in FIG. 5, plunger 102 has a notch 501 oriented axially along at least one of the ridges 109. Notch 501 is an example of a first locking mechanism element. The notch 501 may be a rectangular notch, a V-shape, a U-shape, or other conventional notch geometries of various sizes.

Figure 6:
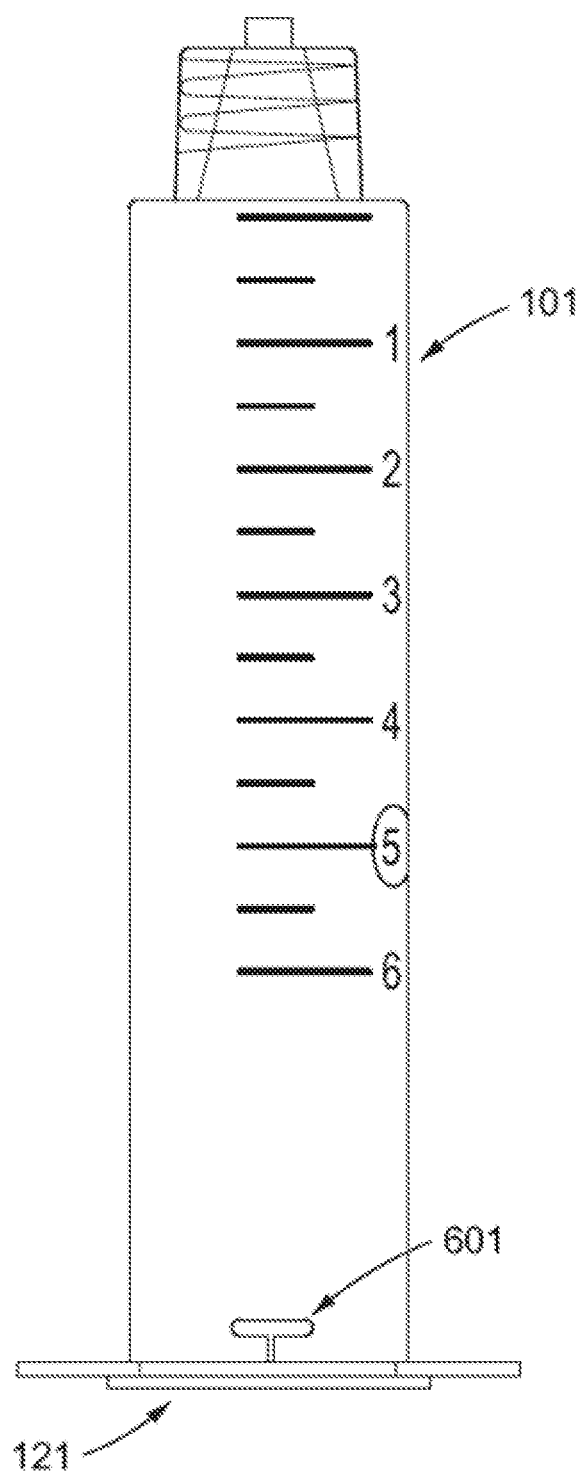
FIG. 6 is a cross-section view of a barrel with a second locking mechanism element along the interior surface of the barrel, according to certain embodiments.
Figure 7:
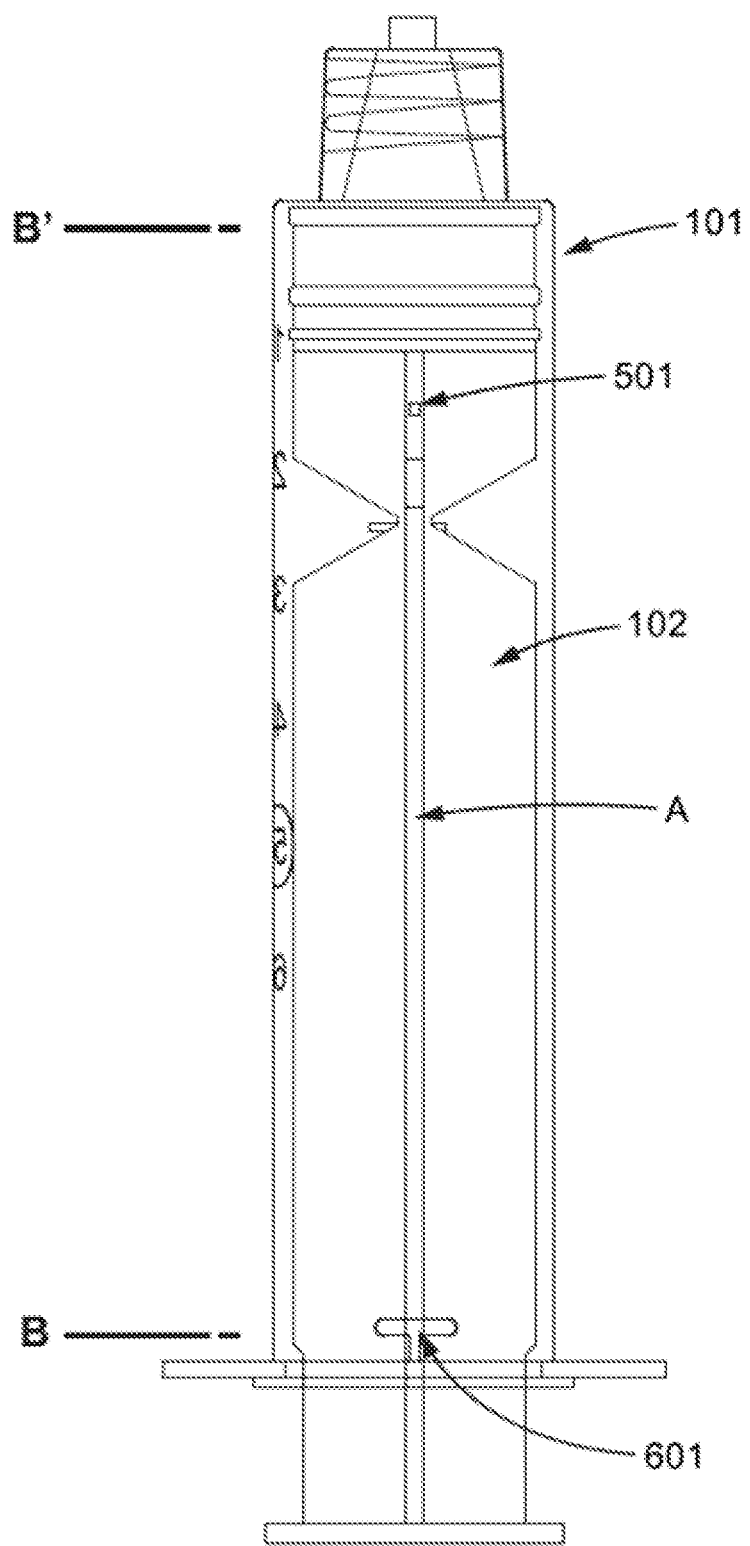
FIG. 7 is a cross-section view of a syringe with the plunger in a fourth position, at which position, the first locking mechanism element and the second locking mechanism element are not engaged, according to certain embodiments.
Figures 8A, 8B:
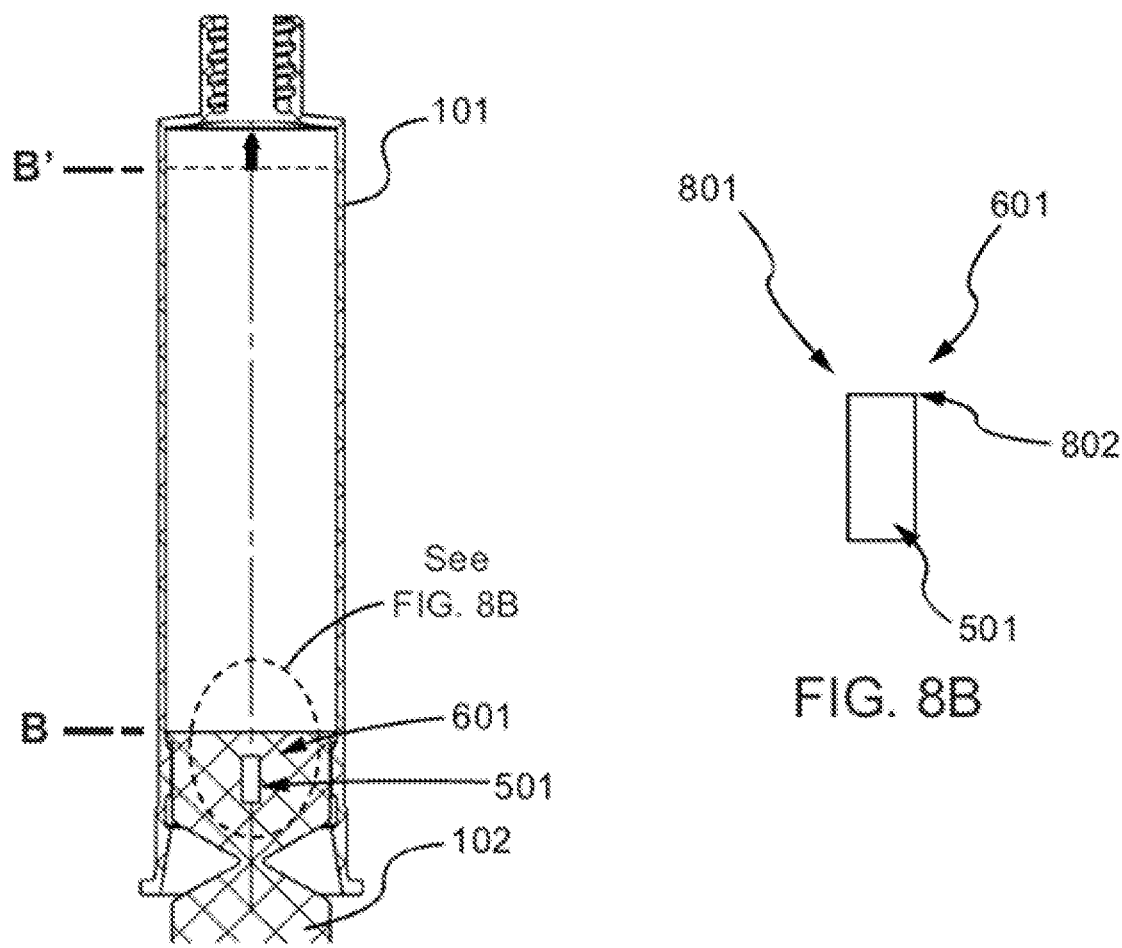
FIG. 8A is a cross-section view of a syringe with the plunger in a fifth position, at which position, the first locking mechanism element and the second locking mechanism element are engaged to restrict movement of the plunger, according to certain embodiments.
FIG. 8B is an enlarged cross-section of a portion of FIG. 8A illustrating the locking mechanisms engaged, according to certain embodiments.

FIG. 6 shows a barrel 101 with a T-shaped slot 601 opening along the interior surface 104 of the barrel 101 near the distal end 114 of the barrel 101. T-shaped slot 601 is an example of a second locking mechanism element. T-shaped slot 601 may contain at least two barbs or one way catches (803, 804), which are an example of a catch section formed at opposite ends along the perpendicular axis of T-shaped slot 601, near the bottom part 802 of T-shaped slot 601 (as defined below). The barbs or one way catches (803, 804 as shown in FIG. 8E) may allow notch 501 to slide vertically in one direction towards the distal end 114 of the barrel 101. Further, the dimension of the T-shaped slot 601 opening may be of different sizes to accommodate different sized cannulas.

As shown in FIG. 4, after cannula tip 119 has been pulled into cavity of barrel 101, plunger 102 may be rotated about (around) the central axis A of the barrel 101 until the notch 501 is oriented axially with T-shaped slot 601. Notch 501 may then enter the top portion 801 (as shown in FIG. 8D) of the T-shaped slot 601, where its movement may be restricted to a latitudinal width (horizontal dimension) of the top portion 801. Latitudinal width of the top portion 801 is defined by opposite ends of top portion 801 and is measured along a latitudinal direction perpendicular to central axis A of plunger 102. T-shape slot 601 further comprises bottom part 802 which extends perpendicularly from top portion 801. With continued rotation of plunger 102 about central axis A, notch 501 travels along the latitudinal width of the top portion 801 and becomes aligned with bottom part 802 of the T-shaped slot 601. When notch 501 is aligned with bottom part 802, plunger 102 may then be pulled vertically (first end of plunger pulled towards the distal end 114 of the barrel 101) until the notch 501 enters the bottom part 802 of the T-shaped slot 601 and engages the barb or one-way catches (803, 804) that may prevent notch 501 (and hence the plunger 102) from being pushed back into the barrel 101. Opposite edges of top portion 801 and bottom part 802 define a length of T-shaped slot 601. The length of T-shaped slot 601 is parallel to central axis A of plunger 102. Latitudinal width of the top portion 801 and the length of T-shaped slot 601 are each greater than a longitudinal length of notch 501. The longitudinal length of notch 501 is defined by opposite ends of notch 501. The longitudinal length of notch 501 is parallel to central axis A of plunger 102.

Referring again to FIG. 4, cannula 105 has longitudinal length Ln from cannula tip 119 to cannula base 107. Longitudinal length Ln runs along longitudinal central axis 118' of cannula 105. A cannula storage portion of the cavity of the barrel 101 extends from shoulder wall 111 to first flat area 121. The cannula storage portion of the cavity of the barrel 101 has longitudinal length Lb that is greater than longitudinal length Ln. Longitudinal length Lb may be parallel to central axis A of barrel medial segment 113.

From the foregoing, it will be appreciate that syringe 100 is adapted to contain cannula 105 in the barrel 101 after injection, and adapted to restrict the movement of the plunger 102, to avoid potential or accidental needle penetration of barrel shoulder wall 111. This provides an additional layer of safety to the off-axis tilt of cannula 105.

The locking mechanism, comprising the T-shaped slot 601 and notch 501 may, in non-limiting aspects, be integral parts of barrel 101 and plunger 102, respectively. Thus, the locking mechanism may be implemented without additional parts, thereby reducing production complexity and cost. In addition, syringe 100 allows for the use of cannulas (e.g., needles) of different sizes and thus different clinical applications.

Another potential advantage of the T-shaped slot 601 is ease of manufacture. A common manufacturing method for syringes is injection molding, where a male-female mold is used to produce the barrel. Slight modifications can be made to an existing male portion of the mold to enable automated production of the T-shaped slot 601. By modifying an existing mold, a manufacturer may avoid having to purchase a new mold or to implement a secondary operation to the T-shaped slot 601 in the barrel.

Figure 9:
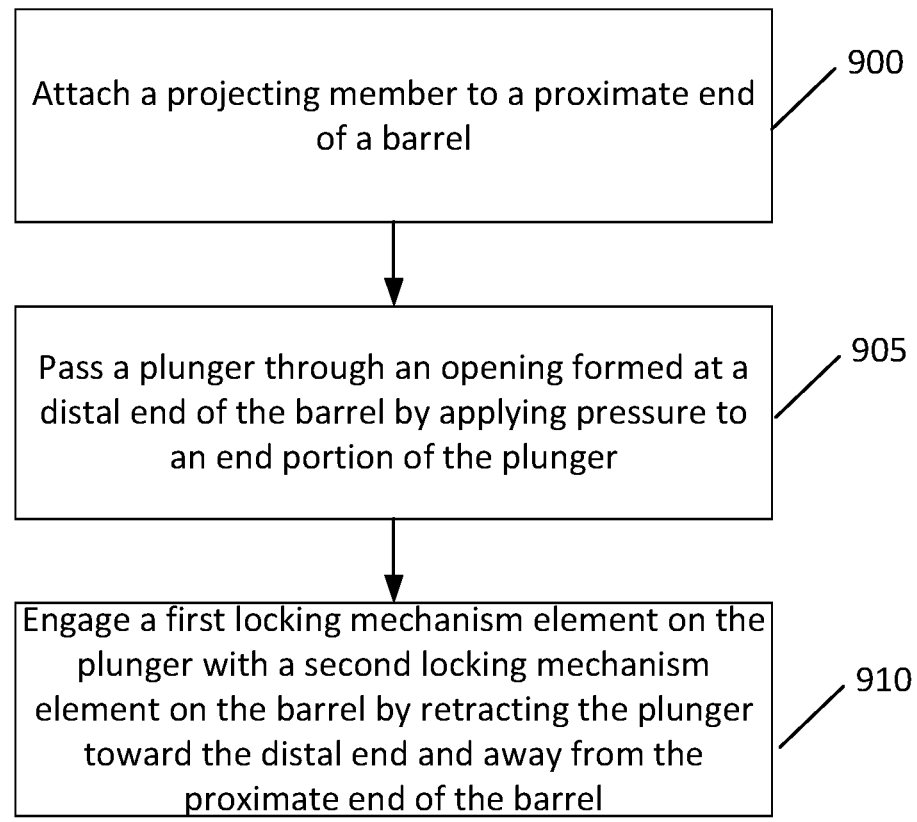
FIG. 9 illustrates a flow diagram of a method, according to certain embodiments.

FIG. 9 illustrates a flow diagram according to certain embodiments. In particular, the method may include, at 900, attaching a projecting member to a proximate end of a barrel. The method may also include, at 905, passing a plunger through an opening formed at a distal end of the barrel by applying pressure to an end portion of the plunger. In addition, the method may include, at 910, engaging a first locking mechanism element on the plunger with a second locking mechanism on the barrel by retracting the plunger toward the distal end and away from the proximate end of the barrel.

According to certain embodiments, the method may also include pushing the plunger from a first position at which the first locking mechanism element is oppositely facing the second locking mechanism element, to a second position after delivery of a content of the barrel at which the cannula is retracted into the barrel at an angle out of alignment with an opening at the proximate end, then to a third position at which the plunger is rotated about a central axis of the plunger. According to other embodiments, engaging the first locking mechanism element with the second locking mechanism element may include rotating the plunger within the barrel until the first locking mechanism element engages with the second locking mechanism element. According to certain embodiments, engaging the first locking mechanism element with the second locking mechanism element may also include pulling the end portion of the plunger vertically away from the distal end of the barrel until the first locking mechanism element engages two catch sections formed along an external perimeter of the second locking mechanism element. In other embodiments, the movement of the plunger, when the second locking mechanism element engages the first locking mechanism element and the two catch sections, may be restricted to a region within the first locking mechanism element.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A syringe, comprising:
   a barrel comprising a distal end, a proximate end, and a second locking mechanism element at the distal end;
   a projecting member configured for attachment to the proximate end of the barrel; and
   a plunger comprising a first locking mechanism element configured to engage with the second locking mechanism element to secure the plunger from moving in the barrel,
   wherein the second locking mechanism element comprises two catch sections formed along an external perimeter of the second locking mechanism element,
   wherein each of the two catch sections open in a single direction towards the distal end,
   wherein the second locking mechanism element is a T-shaped slot,
   wherein the T-shaped slot comprises a first portion oriented in a longitudinal length direction parallel to a central axis of the plunger,
   wherein the T-shaped slot comprises a second portion oriented in a latitudinal width direction of the plunger, and perpendicular to the central axis of the plunger, and
   wherein the two catch sections are fixed to the external perimeter of the first portion, and are positioned opposite of each other with respect to the central axis of the plunger.

2. The syringe according to claim 1, wherein the barrel further comprises:
   a medial segment between the distal end and the proximate end; and
   an interior surface extended from the distal end to the proximate end;
   wherein the first locking mechanism element is attached to a surface of the plunger, and
   wherein the barrel defines an opening at the proximate end.

3. The syringe according to claim 1, wherein the projecting member further comprises:
   a cannula base;
   a cannula mounted on the cannula base; and
   a projective cap covering the cannula, the cannula base, and the projecting member.

4. The syringe according to claim 3, wherein the cannula base comprises a cylindrical cavity.

5. The syringe according to claim 3, wherein the cannula comprises a needle tip and a needle base.

6. The syringe according to claim 5,
wherein the cannula comprises a longitudinal length from the needle base to the needle tip, and
wherein the longitudinal length from the needle base to the needle tip is less than a longitudinal length of the barrel.

7. The syringe of claim 1,
wherein the plunger comprises a plurality of ridges, and
wherein the second locking mechanism element is disposed along a surface of at least one of the plurality of ridges.

8. The syringe according to claim 1, wherein the plunger is sized to pass through an opening formed at the distal end of the barrel when pressure is applied to the second end.

9. The syringe according to claim 1, wherein the plunger is configured to be pushed from a first position at which the first locking mechanism element is oppositely facing the second locking mechanism element, to a second position after delivery of a content of the barrel at which the cannula is retracted into the barrel at an angle out of alignment with an opening at the proximate end, then to a third position at which the plunger is rotated about a central axis of the plunger.

10. The syringe according to claim 1,
wherein a length of the first portion is greater than a longitudinal length of the first locking mechanism element.

11. The syringe according to claim 1,
wherein a width of the second portion is greater than a longitudinal length of the first locking mechanism element.

12. A method of operating a syringe, comprising:
attaching a projecting member to a proximate end of a barrel;
passing a plunger through an opening formed at a distal end of the barrel by applying pressure to an end portion of the plunger; and
engaging a first locking mechanism element on the plunger with a second locking mechanism element on the barrel by retracting the plunger toward the distal end and away from the proximate end of the barrel,
wherein engaging the first locking mechanism element with the second locking mechanism element comprises:
rotating the plunger within the barrel until the first locking mechanism element engages with the second locking mechanism element; and
pulling the end portion of the plunger vertically away from the distal end of the barrel until the first locking mechanism element engages two catch sections formed along an external perimeter of the second locking mechanism element,
wherein the movement of the plunger, when the second locking mechanism element engages the first locking mechanism element and the two catch sections, is restricted to a region within the second locking mechanism element,
wherein each of the two catch sections open in a single direction towards the distal end,
wherein the second locking mechanism element is a T-shaped slot,
wherein the T-shaped slot comprises a first portion oriented in a longitudinal length direction parallel to a central axis of the plunger,
wherein the T-shaped slot comprises a second portion oriented in a latitudinal width direction of the plunger, and perpendicular to the central axis of the plunger, and
wherein the two catch sections are fixed to the external perimeter of the first portion, and are positioned opposite of each other with respect to the central axis of the plunger.

13. The method of operating the syringe according to claim 12, wherein the projecting member comprises:
a cannula base;
a cannula mounted on the cannula base; and
a projective cap covering the cannula, the cannula base, and the projecting member.

14. The method of operating the syringe according to claim 13, further comprising pushing the plunger from a first position at which the first locking mechanism element is oppositely facing the second locking mechanism element, to a second position after delivery of a content of the barrel at which the cannula is retracted into the barrel at an angle out of alignment with an opening at the proximate end, then to a third position at which the plunger is rotated about a central axis of the plunger.

15. The method of operating the syringe according to claim 13, wherein the cannula base comprises a cylindrical cavity.

16. The method of operating the syringe according to claim 13, wherein the cannula comprises a needle tip and a needle base.

17. The method of operating the syringe according to claim 13,
wherein the cannula comprises a longitudinal length from the needle base to the needle tip, and
wherein the longitudinal length from the needle base to the needle tip is less than a longitudinal length of the barrel.

* * * * *